(12) United States Patent
Michalek et al.

(10) Patent No.: US 8,834,809 B2
(45) Date of Patent: Sep. 16, 2014

(54) SOLID WASTE COMPRESSION LOADING AND WASTE TREATMENT APPARATUS AND METHOD

(71) Applicant: Estech USA, LLC, Canal Winchester, OH (US)

(72) Inventors: Jan K. Michalek, Pataskala, OH (US); Theodore J. Thomas, Columbus, OH (US)

(*) Notice: Subject to any disclaimer, the term of this patent is extended or adjusted under 35 U.S.C. 154(b) by 0 days.

(21) Appl. No.: 13/948,731

(22) Filed: Jul. 23, 2013

(65) Prior Publication Data

US 2013/0309143 A1    Nov. 21, 2013

Related U.S. Application Data

(63) Continuation of application No. 12/587,612, filed on Oct. 9, 2009, now abandoned.

(60) Provisional application No. 61/195,791, filed on Oct. 10, 2008.

(51) Int. Cl.
*A61L 11/00* (2006.01)
*A61L 2/07* (2006.01)

(52) U.S. Cl.
CPC .. *A61L 2/07* (2013.01); *A61L 11/00* (2013.01)
USPC ............................. 422/295; 422/292; 422/297

(58) Field of Classification Search
USPC .................................................. 422/292, 307
See application file for complete search history.

(56) References Cited

U.S. PATENT DOCUMENTS

| | | | |
|---|---|---|---|
| 1,026,987 A | 5/1912 | Kardos |
| 2,932,244 A | 4/1960 | Moyer |
| 3,000,295 A | 9/1961 | Fenton |
| 3,266,096 A | 8/1966 | Thomas et al. |
| 3,545,369 A | 12/1970 | Tokushima |
| 3,564,993 A | 2/1971 | Tezuka |
| 3,965,812 A | 6/1976 | Oberg |
| 3,987,615 A | 10/1976 | Hill, Jr. |
| 3,996,849 A | 12/1976 | Del Jiacco |
| 3,999,476 A | 12/1976 | Thompson |
| 4,040,230 A | 8/1977 | Pessel et al. |
| 4,041,856 A | 8/1977 | Fox |
| 4,059,049 A | 11/1977 | Tillgren |
| 4,121,515 A | 10/1978 | Tea |
| 4,129,070 A | 12/1978 | Kaffka |
| 4,148,255 A | 4/1979 | McQueen |
| 4,161,911 A | 7/1979 | Schafer et al. |
| 4,201,129 A | 5/1980 | Matthys |

(Continued)

FOREIGN PATENT DOCUMENTS

WO       2006/056768 A2    6/2006
WO    WO 2006/121697     * 11/2006

*Primary Examiner* — Sean E Conley
(74) *Attorney, Agent, or Firm* — Standley Law Group LLP

(57) ABSTRACT

The invention includes an apparatus, system, waste treatment facility and method of autoclave loading and treatment that involves (a) receiving solid waste at a solid waste treatment facility; (b) compressing the waste into a plurality of compressed bales, the compressed bales bound by a binding material adapted to melt at a temperature at which an autoclave operates or otherwise break upon the operation of the autoclave; (c) loading the compressed bales into an autoclave; and (d) operating the autoclave so as to melt or break the binding material to allow the compressed bales of solid waste to be decompressed and treated in the autoclave.

9 Claims, 3 Drawing Sheets

(56) References Cited

U.S. PATENT DOCUMENTS

| | | |
|---|---|---|
| 4,337,694 A | 7/1982 | Brown |
| 4,413,555 A | 11/1983 | Swinney |
| 4,463,669 A | 8/1984 | Van Doorn et al. |
| 4,476,779 A | 10/1984 | Hasebe et al. |
| 4,534,302 A * | 8/1985 | Pazar ............ 110/346 |
| 4,540,495 A | 9/1985 | Holloway |
| 4,594,942 A | 6/1986 | Denneboom |
| 4,658,719 A | 4/1987 | Jackson et al. |
| 4,787,308 A | 11/1988 | Newsom et al. |
| 4,936,206 A | 6/1990 | Miles et al. |
| 4,961,375 A | 10/1990 | Weder et al. |
| 5,006,029 A * | 4/1991 | Galgana ............ 414/327 |
| 5,007,337 A | 4/1991 | Newsom |
| 5,044,271 A | 9/1991 | Robbins et al. |
| 5,081,922 A | 1/1992 | Rudd, Jr. et al. |
| 5,170,702 A | 12/1992 | Schwelling |
| 5,181,950 A | 1/1993 | Kneer |
| 5,193,454 A | 3/1993 | Bollegraaf |
| 5,195,429 A | 3/1993 | Firpo |
| 5,201,266 A | 4/1993 | Schmalz et al. |
| 5,236,603 A | 8/1993 | Sampson |
| 5,279,441 A | 1/1994 | Featherall |
| 5,353,698 A | 10/1994 | Robbins |
| 5,421,252 A | 6/1995 | Reichel |
| 5,472,997 A | 12/1995 | Koslowski et al. |
| 5,558,014 A | 9/1996 | Robinson |
| 5,687,643 A | 11/1997 | Felts et al. |
| 5,732,617 A | 3/1998 | Lollini |
| 5,816,141 A | 10/1998 | Aylsworth et al. |
| 5,832,815 A | 11/1998 | Bollegraaf |
| 5,845,568 A | 12/1998 | Rosser, Jr. |
| 6,196,124 B1 | 3/2001 | Schaeffer |
| 6,468,019 B1 | 10/2002 | Duval |
| 6,499,931 B1 | 12/2002 | Garrett, Jr. et al. |
| 6,694,871 B1 | 2/2004 | Wildes et al. |
| 6,729,229 B1 | 5/2004 | Wildes et al. |
| 6,823,776 B1 | 11/2004 | Olds |
| 2002/0148366 A1 | 10/2002 | Sutton et al. |
| 2008/0206094 A1 * | 8/2008 | Holloway ............ 422/20 |

* cited by examiner

SOLID WASTE COMPRESSION LOADING AND WASTE TREATMENT APPARATUS AND METHOD

RELATED APPLICATION DATA

This application claims the priority benefit of U.S. Provisional Application Ser. No. 61/195,791, filed Oct. 10, 2008, which is hereby incorporated in its entirety by reference.

TECHNICAL FIELD

The present invention relates to the treatment of municipal solid waste ("MSW") and the like. This invention disclosure presents a means of loading an autoclave and utilizing steam to heat and dry wet solids inside a rotating vessel.

BACKGROUND OF THE INVENTION

A waste autoclave is a form of solid waste treatment that utilizes heat, steam and pressure of an industrial autoclave in the processing of waste. Saturated steam is pumped into the autoclave at elevated temperatures. The pressure in the vessel is maintained for a temperature-dependent period to allow the process to fully 'cook' the waste. The autoclave process provides an effective pathogen and virus kill.

The 'cooking' process causes plastics to soften and flatten, paper and other fibrous material to disintegrate into a fibrous mass, bottles and metal objects to be cleaned, and labels etc. to be removed.

Rotating waste autoclaves provide mechanical forces to further process the waste. With rotation, the cellulose fibers (in paper, cardboard, and yard wastes) are mechanically and thermally pulped, analogous to the process known as thermo-mechanical pulping in the pulp and paper industry.

After 'cooking', the steam flow is stopped and the pressure vented. When depressurized, the autoclave door is opened, and by rotating the drum the 'cooked' material can be discharged and safely and easily separated by a subsequent series of screens and recovery systems. Consequently, a waste autoclave system can serve as a functional alternative to landfills, providing benefits of recycling of clean and sterile materials recovered from municipal wastes.

A basic invention for municipal waste autoclaves is found in U.S. Pat. No. 4,540,495 (Holloway, 1985) and is now in the public domain which is hereby incorporated herein by reference.

The present invention represents an improvement over prior art apparatus and methods, such as those described in U.S. Pat. Nos. 5,540,391; 5,126,363; 5,253,764; 5,190,226; 5,361,994; 5,427,650; 5,407,809; 5,636,449; 5,655,718 and 6,397,492, all of which are hereby incorporated herein by reference. PCT application PCT/US06/16773 and co-pending patent application Ser. No. 11/716,101 are also hereby incorporated herein by reference.

The cost performance of an autoclave is driven predominantly by throughput, which in turn is determined by the density to which vessels can be loaded. Practitioners to date have used a variety of methods to load vessels, ranging from loose feed systems (e.g., conveyors) to light duty compression systems (compressing conveyors) to heavy-duty compression systems (compaction and load). Systems to date have not solved the core problem, which is to rapidly load an autoclave, preferably while rotating, with a designed or pre-determined load of material.

In expansion of this core problem, MSW typically arrives on a "tipping" floor as a compacted mass. This compacted mass is broken apart and larger salvageable items are recovered. Waste materials expand in volume during the recovery.

In autoclave system processing, waste is moved by conveyor from the tipping floor to the processing floor. Waste may move more or less continuously after the tipping floor begins operations, while waste is charged into a vessel over a much shorter period. Thus, it is desirable to provide a "warehousing" activity and facility to store and accumulate waste over an hour or so, and then release it much more rapidly for load-out into a vessel.

Vessels are typically designed to operate within a 5-40% of full volume load range. Typically, an initial load will see significant volume reduction during vessel operations. Thus it is possible to compress the waste prior to or during the loading process, while still resulting in a partially filled vessel (on the basis of volume) after processing.

The economics of a system are driven by throughput. It is therefore desirable to operate a vessel near its upper design load, rather than near its lower design load. In order to achieve the upper design load, the load must be compressed prior to and/or during the loading process.

Prior practitioners have found pre-compression and/or in vessel compression difficult to achieve in practice because, once released from pressure, waste expands rapidly. Further, compression during the loading process requires significant time that could otherwise be used in waste processing.

SUMMARY OF THE INVENTION

One of the key aspects of the present invention is the use of a separate waste compressor/baler, preferably operating during the time window of the vessel processing, so as to "debottleneck" the waste compression/loading process.

Waste may pre-densified using any of a number of standard or modified compactors, the list including hay bailers, trash compactors, and MSW compactors. The bales may be cubic, spherical, rectangular, or cylindrical, and of any size that is convenient for loading into a vessel. The bales may be produced more or less continuously, such as in a continuous batch process, and then warehoused for later use, preferably on site. Upon demand, warehoused bales are retrieved and dispatched into the vessel(s) using standard conveying equipment.

One of the important features of the invention, is the use of baling materials and wraps that fail in the high temperature/high steam pressure environment of the vessel as the temperature approaches 300 F or higher. For example, the melting point of LDPE/HDPE film is ~260 F. The film, once melted in the vessel, forms balls of plastic that can be separated for recycle.

This present invention provides improvements in the functionality of waste autoclave systems by increasing loading efficiency and overall throughput efficiency.

Another benefit of using a film-baled pre-compressed waste is that the waste can be baled on the tipping floor, and then transported to the vessel area. In a related U.S. Patent Application Ser. No. 61/123,351 (hereby incorporated herein by reference), there is described designs and practices that segregate the clean area of the exit end of the vessel from the non-clean area beginning with the tipping floor. The use of baled wastes extends the clean zone to include the vessel loading area. That is, using baled waste allows one to bring the waste directly to the vessel without loose waste being laid in the vessel area.

Another feature of the process of the present invention is that of over-compressing the bales. In order to achieve maximum throughput, preferentially the load is about 30% of full density. However, it is demonstrated technology to be able to routinely compress municipal waste to 60%-90% of full density. The use of overly compressed bales increases the rate at which vessels may be loaded.

In general terms, the invention includes an apparatus, system, waste treatment facility and method of autoclave loading and treatment.

The present invention includes a method of loading solid waste into an autoclave at a solid waste treatment facility and treating the waste, the method comprising: (a) receiving solid waste at a solid waste treatment facility; (b) compressing the waste into a plurality of compressed bales, the compressed bales bound by binding material adapted to melt at a temperature at which an autoclave operates or otherwise to break upon the operation of the autoclave; (c) loading the compressed bales into an autoclave; and (d) operating the autoclave so as to melt or break the binding material to allow the compressed bales of solid waste to be decompressed and treated in the autoclave.

The present invention also includes a method of operating an autoclave comprising the steps of obtaining a plurality of compressed bales of waste, the compressed bales bound by a material adapted to melt at a temperature at which an autoclave operates or otherwise to break upon the operation of the autoclave; and loading the compressed bales into an autoclave. This method is then followed by operating the autoclave so as to melt or break the binding material to allow the compressed bales of solid waste to be decompressed and treated in the autoclave.

The present invention thus includes a baling process, whereby the baling material (not limited to strapping and wrapping) is constituted of a material that is designed to yield and fail at vessel operating conditions, thereby releasing bale contents after the autoclave is loaded and/or after its doors are sealed and the autoclave operated under steam. This process neatly averts the problems of pre-compression or in-vessel compression found by others. The failure mechanism may be thermal, but other vessel conditions could be used to initiate a failure.

The compression bales of the present invention may be made through the use of any baling equipment that may be adapted to using binding material as described herein, such as those described in the following U.S. Pat. Nos. 3,996,849; 3,999,476; 4,041,856; 4,121,515; 4,129,070; 4,148,255; 4,161,911; 4,463,669; 4,658,719; 5,007,337; 5,044,271; 5,081,922; 5,170,702; 5,279,441; 5,558,014; 5,732,617; 5,816,141; 5,845,568; 6,468,019; 6,499,931; and 6,823,776 which are hereby incorporated herein by reference.

It is preferred that an additional plurality of compressed bales is prepared while the autoclave is operating, to efficiently reduce delays between operation cycles. These bales typically and preferably are stored at the solid waste treatment facility prior to loading.

The present invention also includes a process whereby waste streams are compression baled and optionally stockpiled prior to processing in an autoclave vessel, thereby allowing the process equipment operations to be decoupled from the waste supply operations.

It is also preferred that the solid waste treatment facility comprises a conveyor, and that the plurality of compressed bales is stored on the conveyor mechanism prior to loading. The process in accordance with one embodiment of the present invention features the stockpiling on one or more conveyor belts used to transfer bales to the vessel, so as to have a number or bales poised to be rapidly injected into the autoclave. The conveyor may be operated at relatively high speed, such that the full complement of bales may be injected into the autoclave within a time frame of a matter of a few minutes (i.e., such as less than 5 minutes), and indeed may be operated at such high speeds that allow a full complement of bales to be injected into the autoclave in less than 60 seconds, and even well less than 30 seconds.

The binding material may be selected from the group consisting of strapping and wrapping materials that are of such material and thickness to hold the baled waste in place under compression, while being amenable to disintegration under autoclave rotation or operating conditions, such as those selected from the group consisting of polyethylenes. The present invention thus includes a baling and autoclaving process whereby the temperature range of the vessel is substantially in excess of 260 F, preferably 300-340 F, so as to rapidly melt polyethylene (and other low melting point) baling material, such as baling strands, straps, films and the like.

The compressed bales are charged into the autoclave through application of mechanical forces, such as through conveyor belt action or other mechanical force that throws the compressed bales into the autoclave. The present invention also includes an apparatus and process in accordance with which the vessel feeding conveyor belt is a high speed belt and/or is provided with a "thrower" to rapidly move the bales into the vessel.

It is preferred that the autoclave is disposed at an angle to the horizontal so as to assist in the loading of the bales, and it is also preferred that the autoclave is rotated during loading so as to assist in the loading of the compressed bales.

The invention also includes a system for loading solid waste into an autoclave at a solid waste treatment facility and treating the waste, the system comprising: (a) an autoclave; and (b) a baling apparatus adapted to compress the waste into a plurality of compressed bales, the bales bound by a material adapted to melt at a temperature at which the autoclave operates; and (c) a conveyor adapted to load the bales of waste into the autoclave.

The present invention may be adapted to operate with any autoclave system, such as those known and used in the art, autoclaves that are held permanently at an angle, or those that may be tilted from the horizontal are preferred owing to the loading system featured in the present invention.

The conveyor additionally preferably comprises a conveyor belt and a mechanical forcing arrangement for rapidly and positively charging the bales into the autoclave. The autoclave most preferably is disposed at an angle to the horizontal so as to assist in the loading of the bales, and is rotated during loading so as to assist in the loading of the bales. It is preferred that the conveyor, or at least its loading terminal segment, is linear and faces directly into the autoclave in order to the speed loading.

In a preferred embodiment, the conveyor has a loading end and a discharge end, and there is a barrier disposed between the conveyor loading end and the conveyor discharge end, such that the conveyor extends through the barrier. The barrier may be part of an entire chamber holding the autoclave so as to better separate and maintain the area of the autoclave as a clean area.

In a preferred embodiment, an additional plurality of compressed bales may be prepared while the autoclave is operating. It is preferred that the plurality of compressed bales be stored at the solid waste treatment facility prior to loading, typically adjacent to or part of the building or building complex that houses the autoclave. The plurality of compressed bales next to be loaded may be stored on the conveyor mechanism prior to loading.

The binding material may be selected from the group consisting of strapping and wrapping materials, and preferably includes polyethylene and polyethylene materials.

The compressed bales are typically charged into the autoclave through application of mechanical forces, and preferably may be thrown into the autoclave or otherwise injected into the autoclave through the application of inertial forces.

The autoclave is preferably disposed at an angle to the horizontal so as to assist in the loading of the bales. Preferably, the autoclave is rotated during loading so as to assist in the loading of the compressed bales.

The invention further includes a solid waste treatment facility for storing solid waste containing a system for loading solid waste into an autoclave at a solid waste treatment facility and treating the waste, the system comprising: (a) a building containing a system for loading solid waste into an autoclave for treatment, comprising: (i) an autoclave; (ii) a baling apparatus adapted to compress the waste into a plurality of compressed bales, the bales bound by a material adapted to melt at a temperature at which the autoclave operates; and (iii) a conveyor adapted to load the bales of waste into the autoclave; and the building containing a storage area for containing a plurality of compressed bales while the autoclave is operating.

Preferably, the building comprises a tipping floor area for receipt of solid waste from trucks, as well as a storage area for the compressed bales.

The facility and process preferably allows for the waste to be compression baled on the tipping floor, thereby allowing the entire vessel area to be a clean zone, if desired. In a preferred embodiment, there may be provided a barrier between the tipping floor area and the autoclave, with the conveyor extending from the tipping floor through the barrier to the autoclave, in order to better isolate the autoclave area as a clean area.

A solid waste treatment facility for storing solid waste containing a system for loading solid waste into an autoclave at a solid waste treatment facility and treating the waste, the system comprising: (a) a building containing a system for loading solid waste into an autoclave for treatment, the system comprising: (i) an autoclave; (ii) a baling apparatus adapted to compress the waste into a plurality of compressed bales, the bales bound by a material adapted to melt at a temperature at which the autoclave operates; (iii) a conveyor adapted to load the bales of waste into the autoclave; and (iv) the building containing a storage area for containing a plurality of compressed bales while the autoclave is operating.

The building typically and preferably comprises a tipping floor area for receipt of solid waste from trucks. The solid waste treatment facility also preferably features a building comprising a storage area for the compressed bales, or the compressed bales may be stored elsewhere. Most preferably, the building comprises a tipping floor area for receipt of solid waste from trucks, a barrier between the tipping floor and the autoclave, the conveyor extending from the tipping floor through the barrier to the autoclave.

The present invention also includes a method of loading solid waste into an autoclave and treating solid waste therein, the method comprising: (a) providing: (i) an autoclave; and (ii) a conveyor adapted to load the bales of waste into the autoclave, the conveyor holding a plurality of compressed bales, the bales bound by a material adapted to melt at a temperature at which the autoclave operates or otherwise break upon the operation of the autoclave; and (b) loading the compressed bales into an autoclave; and (c) operating the autoclave to melt or break the binding material to allow the compressed bales of solid waste to be decompressed and treated in the autoclave.

The additional and preferred parameters are as otherwise described above.

DETAILED DESCRIPTION OF THE PREFERRED EMBODIMENTS

In accordance with the foregoing summary, the following provides a detailed description of the preferred embodiment, which is presently considered to be the best mode thereof.

Figure 1:
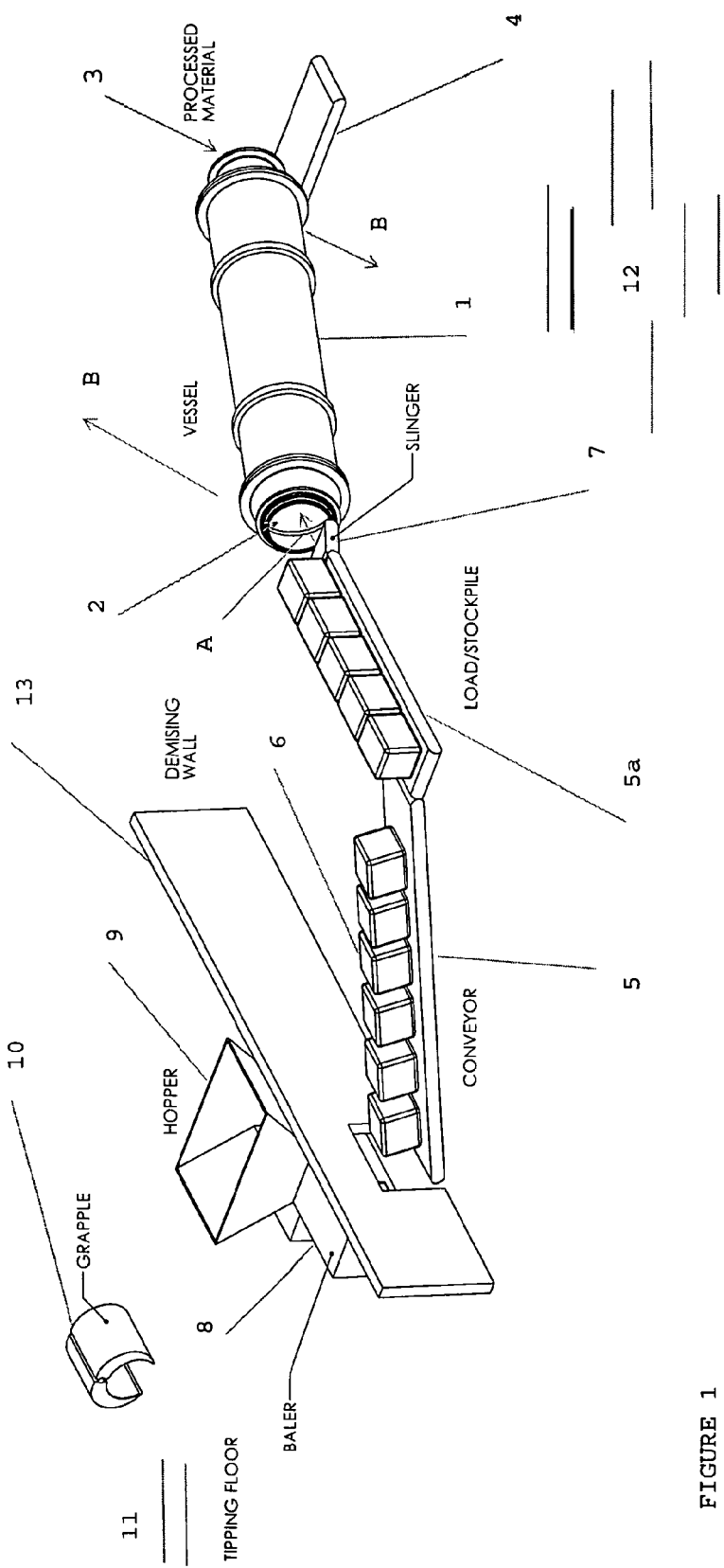
FIG. 1 is a perspective view of a system for processing solid waste products in accordance with one embodiment of the present invention.

FIG. 1 is a perspective view of a system for processing solid waste products in accordance with one embodiment of the present invention. FIG. 1 shows autoclave vessel 1 having input end 2 and an output end 3, each of which is closed by a door (not shown) to form a pressure seal. Output end 3 is served by optional and preferred discharge conveyor 4 that accepts and transports treated waste from the autoclave vessel 1. Input end 2 is served by preferred input conveyor 5 that provides bales of waste 6 for treatment by autoclave vessel 1. As shown in this Figure, the input conveyor 5 may comprise one or more individual conveyor belts, such as load/stockpile conveyor portion 5a. At the end of input conveyor 5 is optional and preferred "thrower" device 7 that serves to throw or kick bales 6 into autoclave vessel 1 in rapid succession during the loading cycle. As an alternative, the load/stockpile conveyor portion 5a may terminate sufficiently close to the input end 2

The bales may be formed off-site, but preferably are formed at the treatment site as shown, such as by baler 8 that is served by hopper 9. Hopper 9 in turn may be provided with loose waste by grapple device 10 that typically takes the loose waste from the tipping floor 11 where it is dumped from trucks or rail cars, and the like.

An inventory of bales 6 may be stored in the tipping floor area in order to have a backlog of bales awaiting transport and processing. These may be stored in the tipping floor area, or in any other area or building conveniently located so as to offer convenient access to the conveyor system.

In a preferred embodiment, the tipping floor area 11, which normally is relatively unsanitary and generates foul odors, may be partially or completely isolated from the environment of the loading/stockpile and treatment area 12 (typically desired to be clean to isolate workers and the treated waste from dirt, dust and odor) by an environmental barrier, such as demising wall through which conveyor 5 may extend. Preferably, the environmental barrier is in the form of a partially or completely enclosed room that contains the loading/stockpile and treatment area 12. Likewise, the tipping floor area 11 may also be partially or completely enclosed in a room.

In operation, a series of bales 6 are created, conveyed to and staged on the latter portion of the conveyor system 5 (i.e., load/stockpile conveyor portion 5a), such as the five bales shown awaiting input into the autoclave vessel 1. The load/ stockpile conveyor portion 5a is preferably oriented in a straight line toward the vessel opening at input end 2. After the autoclave vessel 1 finishes a treatment cycle and is emptied, its output end is closed and its input end 2 is opened. A series of bales 6 (typically calculated to comprise a complete vessel charge), are then conveyed in rapid succession into the autoclave vessel 1. This process may be carried out through the use of a high speed conveyer such as the downstream second leg of conveyor 5 (i.e., load/stockpile conveyor portion 5a). The load/stockpile conveyor portion 5a, which may be pre-loaded with a sufficient number of bales to comprise a full vessel load, preferably may be accelerated to speeds that allow a full vessel load to be placed into the vessel in a matter of seconds. Indeed, the load/stockpile conveyor portion 5a may be accelerated to a speed which injects the bales directly into the vessel opening at input end 2.

FIG. 1 also shows optional slinger mechanism 7 that may be used to jettison the bales in rapid succession into the vessel 1. The mechanism may be in the form of a rapidly actuated hydraulic actuator that throws each of the bales in succession into the vessel 1, such as pivoting in a series of throwing actions as shown in direction arrow A. This may also be done with any equivalent mechanical arrangement, such as those known and used in the art or devices such as kick balers that are able to throw hay bales, and the like. The present invention therefore provides a system that allows for the very rapid loading of baled waste in a form such that the bales may be disintegrated through the normal autoclave processing such as by rotating the vessel and/or supplying it with steam in order to release the waste for further processing.

Figure 2:
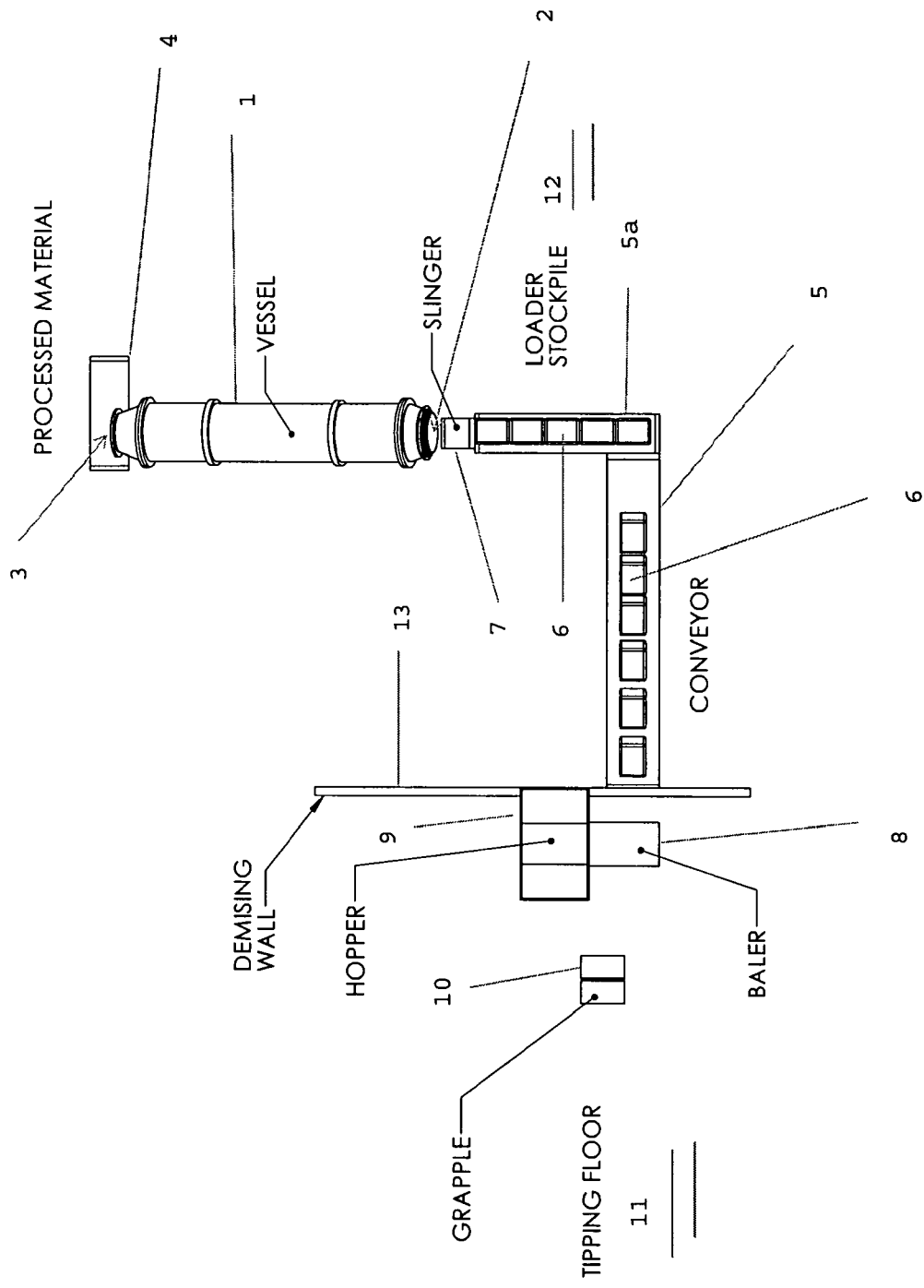
FIG. 2 is a plan view of a system for processing solid waste products in accordance with one embodiment of the present invention.

FIG. 2 is a plan view of a system for processing solid waste products in accordance with one embodiment of the present invention, wherein the same reference numerals are used as in FIG. 1.

Figure 3:
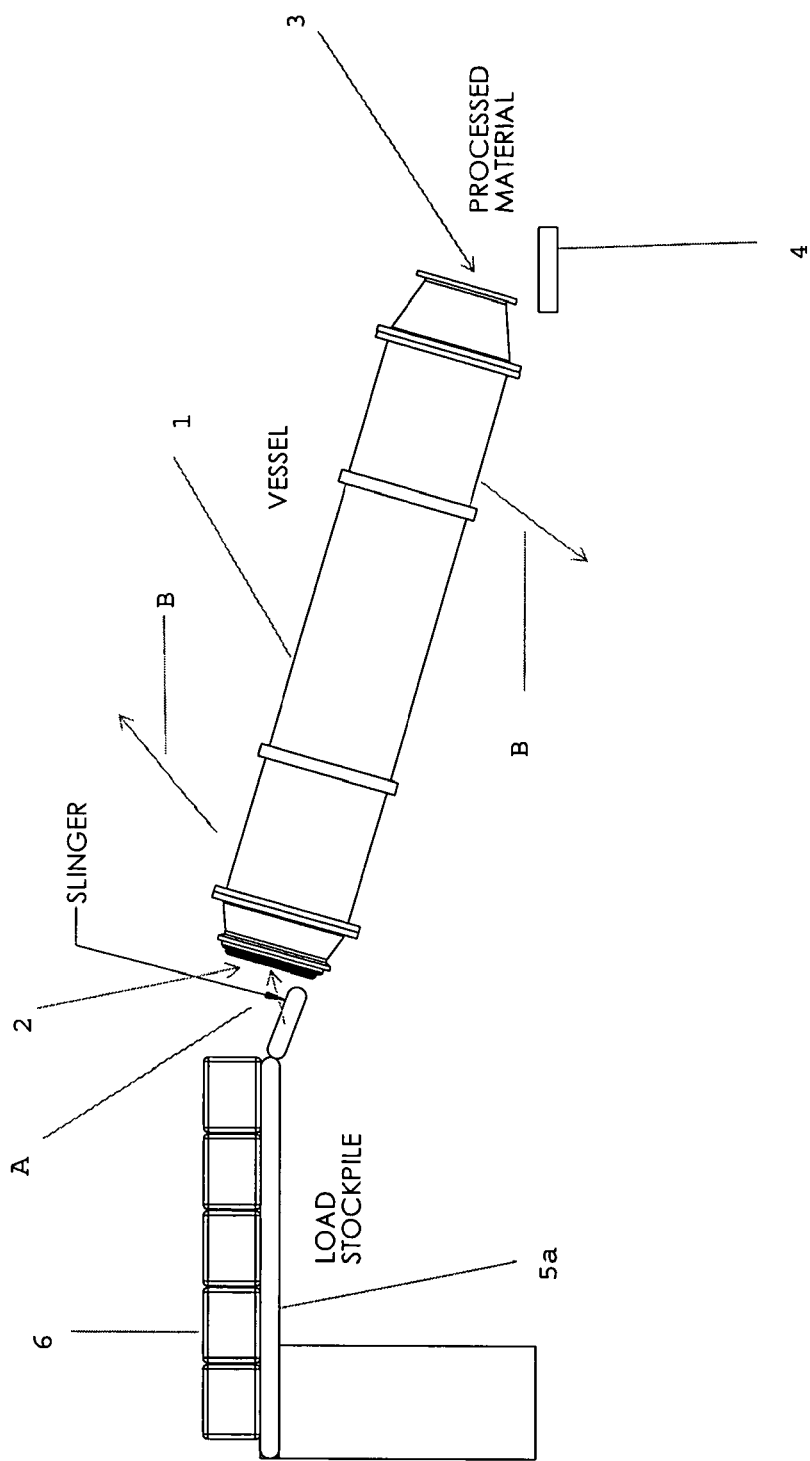
FIG. 3 is partial elevation view of a conveyor and autoclave vessel for processing solid waste products in accordance with one embodiment of the present invention.

FIG. 3 is partial elevation view of a conveyor and autoclave vessel for processing solid waste products in accordance with one embodiment of the present invention, wherein the same reference numerals are used as in FIG. 1.

The vessel 1 may be any type of vessel used in the autoclaving of waste. Preferably, the vessel 1 may have its angle changed with respect to the horizontal in order to best aid loading and unloading, as indicated in direction arrows B in FIGS. 1 and 3.

The operations of the preferred embodiment are described in terms of FIG. 3, the isometric view. Waste is received on a tipping floor 11, which preferably is physically and environmentally separated from the processing room by a demising wall 13. Waste is charged to a hopper 9, using a grapple 10 or other loader. A skilled grapple operator can separate long or heavy items from the bulk of the waste prior to charging the hopper 9. The hopper 9 in turn charges the baler system. The baler operates more or less continuously in accordance with the hopper charging. Products from the baler, consisting of processable Municipal Solid Waste, preferably compressed to a density of 500-1500 pounds per cubic yard (preferentially 1000 pounds per cubic yard), and over-wrapped with a low melting point film such as a polyethylene film, are transported one at a time from the tipping floor 11 via conveyor 5 through the demising wall 13 and to the stockpile/loader area 12. This stockpile/loader conveyor section 5a, which is preferentially horizontal and elevated to the vessel charging height, receives and stockpiles a sufficient number of bales 6 such as to compose one full vessel load. In the preferred embodiment, the stockpile loader is less than 75% of the length of the vessel 1. When the vessel 1 is to be charged, the stockpile/loader conveyor section 5a is activated. At the end of the stockpile/load is a bale slinger 7 to impel the bales 6 into the input opening 2 of the vessel 1. A combination of inertial forces, gravitation forces and physical forces cause the bales to move down the length of the vessel 1, which has been tilted to receive the bales, as shown.

It is apparent that while specific embodiments of the invention are disclosed, various modifications to the apparatus or parameters of the process may be made which will be within the spirit and scope of the invention. Therefore, the spirit and scope of the present invention should be determined by reference to the claims below.

What is claimed is:

1. A system for treating solid waste to neutralize pathogens contained therein, the system comprising:
    a baling apparatus adapted to receive and compress the solid waste into a plurality of compressed bales, each bale bound by a material adapted to melt or break in a temperature range suitable to neutralize the pathogens;
    a rotating waste autoclave, having a loading port at a first end thereof for loading the compressed bales and an unloading port at a second end thereof for unloading loose solid waste devoid of pathogens, the autoclave operating at a temperature in a range of from 260 to 340 F; and
    a conveyor, arranged between the baling apparatus and the loading port of the rotating waste autoclave.

2. A system according to claim 1 wherein said conveyor additionally comprises a conveyor belt and a mechanical forcing arrangement for rapidly and positively charging said bales into said autoclave.

3. A system according to claim 1 wherein said autoclave is disposed at an angle to the horizontal so as to assist in the loading of said bales.

4. A system according to claim 1 wherein said autoclave is rotated during loading so as to assist in the loading of said bales.

5. A system according to claim 1, wherein said conveyor has a loading end and a discharge end, and additionally comprising a barrier disposed between said conveyor loading end and said conveyor discharge end, said conveyor extending through said barrier.

6. A solid waste treatment facility for receiving and treating solid waste to neutralize pathogens contained therein, the facility comprising:
    a baling apparatus adapted to receive and compress the solid waste into a plurality of compressed bales, each bale bound by a material adapted to melt or break in a temperature range suitable to neutralize the pathogens;
    a rotating waste autoclave, having a loading port at a first end thereof for loading the compressed bales and an unloading port at a second end thereof for unloading loose solid waste devoid of pathogens, the autoclave operating at a temperature in a range of from 260 to 340 F;
    a conveyor, arranged between the baling apparatus and the loading port of the rotating waste autoclave; and
    a building, comprising:
        an area for storing the solid waste prior to being compressed in the baling apparatus;
        an area for storing the compressed bales of solid waste before treatment in the autoclave; and
        an area for storing the loose solid waste, devoid of pathogens after treatment in the autoclave.

7. A solid waste treatment facility according to claim 6 wherein said building comprises a tipping floor for receipt of solid waste from trucks.

8. A solid waste treatment facility according to claim 6 wherein said building comprises a storage area for said compressed bales.

9. A solid waste treatment facility according to claim 6 wherein said building comprises a tipping floor for receipt of solid waste from trucks, a barrier between said tipping floor and said autoclave, said conveyor extending from said tipping floor through said barrier to said autoclave.

* * * * *